United States Patent
Mertelmeier

(10) Patent No.: US 7,945,014 B2
(45) Date of Patent: May 17, 2011

(54) X-RAY SYSTEM AND METHOD FOR TOMOSYNTHETIC SCANNING

(75) Inventor: Thomas Mertelmeier, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 12/442,599

(22) PCT Filed: Sep. 26, 2007

(86) PCT No.: PCT/EP2007/060198
§ 371 (c)(1),
(2), (4) Date: Mar. 24, 2009

(87) PCT Pub. No.: WO2008/037731
PCT Pub. Date: Apr. 3, 2008

(65) Prior Publication Data
US 2010/0020920 A1    Jan. 28, 2010

(30) Foreign Application Priority Data
Sep. 29, 2006 (DE) .......... 10 2006 046 741

(51) Int. Cl.
*G01N 23/04* (2006.01)
(52) U.S. Cl. .......... 378/25; 378/21
(58) Field of Classification Search .......... 378/21–27, 378/37, 38–39
See application file for complete search history.

(56) References Cited

U.S. PATENT DOCUMENTS

| | | | |
|---|---|---|---|
| 4,637,040 A | 1/1987 | Sohval et al. | |
| 4,662,379 A | 5/1987 | Macovski | |
| 7,110,490 B2 | 9/2006 | Eberhard et al. | |
| 7,466,795 B2 | 12/2008 | Eberhard et al. | |
| 2007/0223653 A1* | 9/2007 | Ullberg et al. ........... | 378/62 |

FOREIGN PATENT DOCUMENTS
GB    15724241    7/1980

OTHER PUBLICATIONS

"Digital Breast Tomosynthesis Using An Amorphous Selenium Flat Panel Detector," Bissonnette et al, Medical Imaging, Proceedings of SPIE, vol. 5745 (2005) pp. 529-540.
"Quantification For Contrast-Enhanced Digital Breast Tomosynthesis," Caron et al, Medical Imaging, Proceedings of SPIE, vol. 6142 (2006) pp. 61420D-1-61420D-11.

* cited by examiner

*Primary Examiner* — Hoon Song
(74) *Attorney, Agent, or Firm* — Schiff Hardin LLP

(57) ABSTRACT

In an x-ray system and a method for tomosynthetic scanning of a subject, x-ray radiation is emitted from two x-ray sources that are panned along a line relative to the subject during a tomosynthetic scan. The two x-ray sources are located next to each other along the line, and each emit an x-ray beam. X-rays from the two parallel beams attenuated by the subject are detected by a two-dimensional x-ray detector, that is substantially stationary during the tomosynthetic scan.

22 Claims, 2 Drawing Sheets

X-RAY SYSTEM AND METHOD FOR TOMOSYNTHETIC SCANNING

BACKGROUND OF THE INVENTION

1. Field of the Invention

The invention concerns an x-ray system and a method for tomosynthetic scanning of a subject.

2. Description of the Prior Art 3D imaging methods increasingly assert themselves in medical technology. For example, computed tomography (CT), in which an x-ray tube and its opposite detector orbit a patient as an examination subject in order to generate slice exposures of the patient, is hereby a complicated and expensive method. An entire 3D volume is subsequently reconstructed from the slice exposures.

A distinctly less complicated 3D imaging method is digital tomosynthesis, which is in particular developed in connection with mammography. In contrast to CT, an x-ray source is hereby panned around an examination subject as a center of the movement only within a limited angle range, for example ±20° starting from a middle position. An x-ray detector to receive the x-rays hereby remains essentially stationary, i.e. actually stationary, or it is only slightly tilted, for example in order to follow the rotating x-ray tube at least according to the radiation angle. The production of a plurality of x-ray images from respective different angles within the angle region to be panned is designated as tomosynthetic scanning.

Since tomosynthesis should be an optimally cost-effective and uncomplicated method, distinctly simpler (and therefore less resilient) x-ray tubes are hereby used (for example in comparison to CT). The resolution speed of the x-ray tubes is thus limited, and a 50° tomosynthetic scan (i.e. panning of the x-ray tube in an angle range of 50°) for the generation of the multiple x-ray images or projection exposures from various viewing directions today takes between ten seconds and one minute.

A technique known as the dual energy method is also known, in which the subject is exposed twice from each viewing (irradiation) direction with x-ray radiation of two different energies. It is known to execute either two complete scans with a respective energy (i.e. to switch the energy level of the x-ray tube between the two scans) or to execute a single scan and respectively switch the x-ray tube between the two energies in each angle position (i.e. for each projection exposure). The latter also entails a large stress for the x-ray tube (for example in mechanical terms) since both the beam generator and the pre-filtering (swiveling mechanical filter) are switched between two beam qualities.

The scan speed today is normally limited by the x-ray tube since (for example) detectors with fast readout capability (for example 30 images per sec) are used. However, such high image rates can lead to thermal problems in the x-ray tube, not only in the anode but also in the cathode. The thermal problems arise from the need to transport of the heat away from the anode of the x-ray tube since there less than 1% of the supplied energy is converted into x-ray radiation and more than 99% is converted into heat. In contrast to CT with a focal diameter of 1 mm on the anode, due to the higher resolution mammography operates with a 0.3 mm focus, for example, which results in a significantly higher energy density and therefore distinctly greater thermal problems in the x-ray tube.

SUMMARY OF THE INVENTION

An object of the present invention is to provide an improved x-ray system and an improved method for tomosynthetic scanning.

The object is achieved by an x-ray system for tomosynthetic scanning of a subject with an x-ray source unit which emits x-ray radiation for radioscopy of the subject and is panned relative to the subject during the tomosynthetic scanning. The x-ray system has a 2D x-ray detector to acquire the x-ray radiation, which 2D x-ray detector is essentially stationary relative to the subject during the tomosynthetic scan. According to the invention, the x-ray source unit has at least two x-ray sources which are arranged in next to each other. The radiation sources are thus arranged so that they each emit x-rays toward the subject and toward the 2D x-ray detector on different beam paths which intersect in the region of the subject or of the 2D x-ray detector.

The radiation sources can be triggered independently of one another, and thus can be triggered in temporal succession. Due to the corresponding alternating triggering, the thermal load for every single radiation source is halved with the same radiation power or, respectively, image rate of the x-ray system.

By the use of at least two radiation sources, for the same number of x-ray exposures or emission of the same x-ray dose during a tomosynthetic scan each radiation source must emit only a portion of the x-ray radiation (for example half given two radiation sources) relative to a conventional tomosynthetic x-ray system with one radiation source. The number of projections—thus x-ray exposures that can be generated in a given scan time during the tomosynthetic scan—increases. Therefore the scan speed (thus the time for the complete tomosynthetic scanning) can be distinctly reduced given a corresponding, sufficiently fast detector if the x-ray excitations were the critical time factor. Since each radiation source must emit less radiation, the thermal load of the radiation sources likewise drops relative to a single radiation source. The entire beam power of the x-ray system likewise increases with the number of sources.

A thermal unloading of the respective radiation source thus results given an overall equivalent radiation power of the x-ray system, or a correspondingly multiplied beam power of the x-ray system results given the same thermal load of the radiation sources.

The radiation sources can be arranged in a common housing of the x-ray source. All radiation sources can then be panned uniformly or, respectively, simultaneous around the subject as before for the tomosynthetic scan. The design expenditure and the design itself of previous x-ray systems hardly changes, namely only in relation to the inner components of the housing of the x-ray source. The x-ray tubes or radiation sources are pulsed (in activated) alternation.

The radiation sources can be arranged in a single x-ray tube. Known x-ray systems are hereby particularly simple to retrofit in x-ray systems according to the invention; the power circuits only need to be designed for a single x-ray tube, even in an x-ray system according to the invention.

In the case of a single x-ray tube with multiple radiation sources, various anodes for different radiation sources can be contained in the x-ray tube. For example, a separate anode with a respective single focal spot can thus exist for each radiation source. The anodes can hereby already be respectively, specially designed for a specific type of x-ray radiation; for example, both radiation sources can be fashioned for respectively different x-ray spectra.

Alternatively, however, different radiation sources can also be arranged as different focal spots on a single anode. A corresponding x-ray tube with a single anode is simpler and less costly to execute.

As already mentioned, different radiation sources can be configure to emit x-rays of different energies. To implement the dual energy method, each radiation source can be permanently set to a specific energy level of the x-ray power. The single radiation source thus does not need to be continuously switched between different energies. This means significantly less stress for the radiation sources. In connection with an energy-resolving detector, both radiation sources can even be simultaneously excited, and two x-ray images projection exposures with different beam energy can respectively be acquired simultaneously by the detector. The scan time for a dual energy tomosynthetic scan is hereby distinctly reduced. Naturally, as before a switching of the radiation sources over to one location is also conceivable so that one and the same projection acquisition is executed with different energies.

During a tomosynthetic scan, the x-ray source is panned in specifically defined angle increments relative to the subject, and an x-ray image is generated at every angle increment. The distance between two radiation sources can be selected so that it corresponds to the angle increment or, respectively, a multiple of this. By exciting both radiation sources, two projection exposures for the tomosynthetic scan can be generated from one position of the x-ray source. Only the x-ray source must then be displaced again by one or more angle increments. If the radiation sources are offset by a single angle increment, for example, the x-ray source is subsequently offset by double the angle increment and two x-ray exposures are again generated by the different radiation sources at an interval of a single angle increment. The step count for the panning of the x-ray source is thus distinctly reduced relative to a known x-ray system.

However, the offset between the sources can also be half of an angle increment, for example, or, respectively, be executed alternating, for example by one half, then by two, then again by half an angle increment etc. A continuous movement and time-offset pulsing of the radiation sources to realize different scans (i.e. angles for the production of an x-ray image) is conceivable. The radiation sources are thus pulsed in order to send x-ray radiation at the desired angle position and thus to generate a projection exposure.

During the entire tomosynthetic scan, the x-ray source is panned over a whole angle range (for example 50°) relative to the subject. For example, two radiation sources can be arranged so that their interval (the angle between the respective beam axes) corresponds to approximately half of the angle range. The entire x-ray source must then be panned only half of the angle range to cover the entire angle region, wherein each radiation source respectively sweeps across half of the angle range (or somewhat more due to an overlap).

The x-ray system according to the invention is in particular suitable as an x-ray system in a mammography system in which a breast of a patient is tomosynthetically scanned and is subsequently reconstructed in the framework of a tomosynthesis.

With regard to the method, the object is achieved via a method for tomosynthetic scanning of a subject in which x-ray radiation is emitted for radioscopy of a subject by an x-ray source, wherein the x-ray source is panned relative to the subject during the tomosynthetic scan. During the tomosynthetic scan the x-ray radiation is received by an x-ray detector that is essentially stationary relative to the x-ray source. According to the invention, the x-ray radiation is emitted by at least two radiation sources in the x-ray source.

The two radiation sources can be activated independently of each other.

The method according to the invention and the advantages resulting from this were already explained in connection with the x-ray system according to the invention. Additional advantageous embodiments of the method were likewise already explained in connection with the x-ray system according to the invention.

DESCRIPTION OF THE PREFERRED EMBODIMENTS

Figure 1:
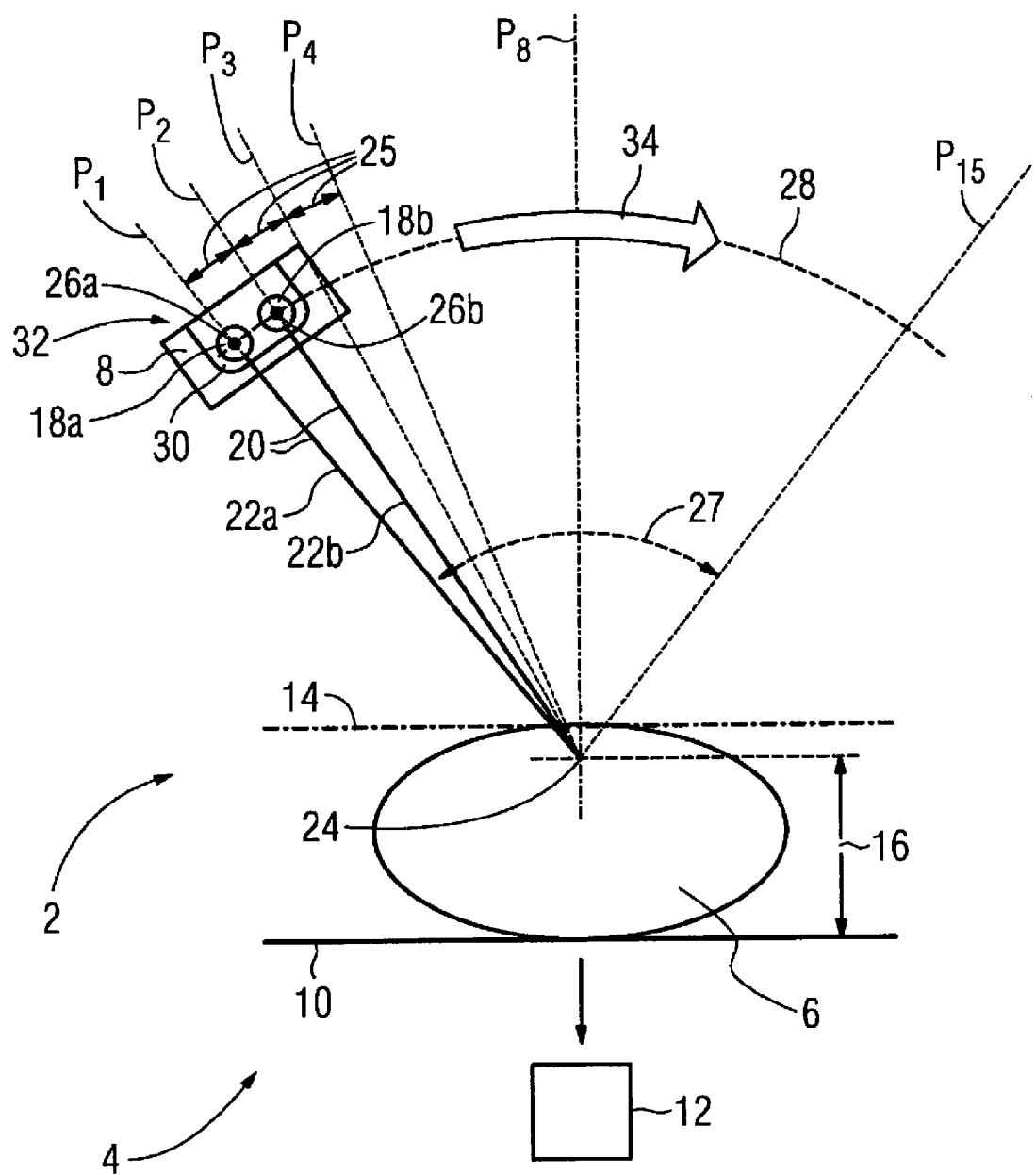
FIG. 1 schematically illustrates an x-ray system for tomosynthetic scanning in mammography, with an x-ray source unit having two x-ray sources in accordance with the present invention.

FIG. 1 shows an x-ray system 2 for tomosynthetic scanning of a female breast 6 fixed in a retention device 4. The x-ray system 2 comprises an x-ray source 8 and a 2D flat panel detector 10 to acquire 2D x-ray images 12. The flat panel detector 10 moreover serves as a first compression plate of the retention device 4 which comprises a second compression plate 14, between which flat panel detector 10 and compression plate 14 the breast 6 is compressed in the direction of the double arrow 16.

The x-ray source 8 comprises two radiation sources 18a,b which respectively emit x-ray radiation 20 in the direction of a center beam axis 22a,b. The center beam axes 22a,b intersect at a point of a pivot axis 24 runs perpendicular to the plane of the drawing in FIG. 1, and therefore inside the breast 6, parallel to the flat panel detector 10 or, respectively, the compression plate 14.

The entire x-ray source 8 can also be panned on this pivot axis 24 so that respective focus points 26a,b of the radiation sources 18a,b run on a line 28 shaped like a circle segment. In FIG. 1, both focus points 26a,b lie as two focal spots on a single anode 30 of an x-ray tube 32 (shown only schematically).

For tomosynthetic presentation of the breast 6, a plurality of x-ray images 12 of this must be generated first. This occurs in the tomosynthetic scan in that x-ray radiation 20 is respectively sent out along one of the projection lines or, respectively, directions $P_1$ through $P_{15}$ towards the flat panel detector 10, and an x-ray image 12 (thus a projection exposure) is generated for each of these projection directions. All projection lines $P_1$-$P_{15}$ are hereby respectively offset by 5° relative to the pivot axis 24 so that, given 15 projection lines, overall a panning range 27 of the x-ray images 12 of 70° results. The respective angle increment 25 for two projection exposures is thus 5° in FIG. 1.

The mammography in FIG. 1 now ensues such that the x-ray source 8 covers the projection lines $P_1$ and $P_2$ through the two focus points 26a,b in the shown position and emits x-ray radiation 20 along these, thus along their center beam axes 22a,b in order to generate two x-ray images 12 one after another in temporal succession. The entire x-ray source 8 is subsequently panned in the direction of the arrow 34 (thus by two angle increments—thus 10°—around the pivot axis 24 in the scan or, respectively, tomosynthetic scan direction) so that the focus points 26a,b come to lie on the projection lines $P_3$ and $P_4$. The radiation sources 18a,b are in turn excited in temporal succession from this position in order to generate two additional x-ray images 12. This process is repeated until the focus point 26b has reached the projection line $P_{15}$ in order to generate the fifteenth (and thus last) x-ray image 12.

Alternatively, a continuous movement of the radiation sources 18a,b is also possible, wherein these are then pulsed at the projection lines $P_{1-15}$ (thus while passing them; pulse-shaped x-ray radiation 20 is thus generated.

Figure 2:
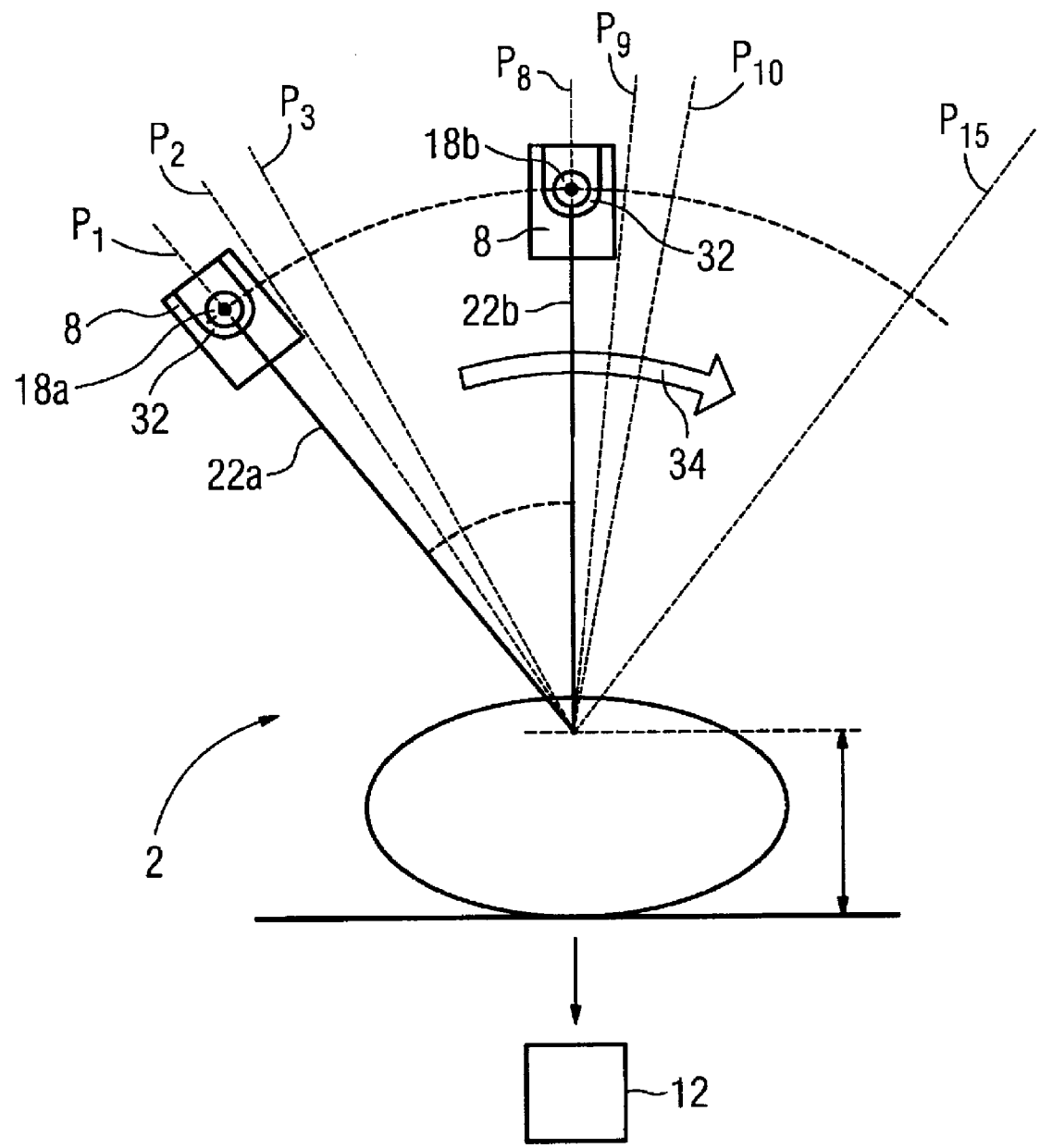
FIG. 2 schematically illustrates an alternative x-ray system in accordance with the present invention, with two separate x-ray units each having one radiation source.

FIG. 2 shows an alternative embodiment of an x-ray system 2 in which both radiation sources 18a,b are mounted in a respective separate x-ray source 8. One x-ray tube 32 is thus located in each x-ray source 8. Relative to FIG. 1, in FIG. 2 the radiation sources 18a,b are spaced significantly farther apart from one another with regard to their central beam axes 22a,b. Namely, overall these encompass an angle of second angle increments, thus 35°. In the situation presented in FIG. 2, the central beam axis 22a with the projection line $P_1$ and the central beam axis 22b with the projection line $P_8$ therefore coincide. The relative angle between two central beam axes 22a,b is hard-set (as in FIG. 1) and thus is not variable during the tomosynthetic scan, for example by installing the two x-ray sources on a common pivot arm (not shown).

In FIG. 2, the radiation sources 18a,b are also initially excited in temporal succession, whereby two x-ray images 12 are created. The two x-ray sources 9 are subsequently synchronously panned, but only by one angle increment (thus 5°), thus half as far as in FIG. 1. The central beam axes 22a,b then coincide with the projection lines $P_2$ and $P_9$. Two x-ray images 12 are now generated again, and the corresponding procedure is repeated until the radiation source 18b again lies on the projection line $P_{15}$. In contrast to FIG. 1, each x-ray source 87 must thus be panned only by 35°, thus half of the total angle range of 70° between the projection lines $P_1$ and $P_{15}$.

Alternatively, in FIG. 1 the radiation sources 18a,b can be designed separately according to FIG. 2.

Although modifications and changes may be suggested by those skilled in the art, it is the intention of the inventor to embody within the patent warranted heron all changes and modifications as reasonably and properly come within the scope of his or her contribution to the art.

I claim as my invention:

1. An x-ray system for tomosynthetic scanning of a subject, comprising:
    two x-ray sources that each emit an x-ray beam, said x-ray beams proceeding toward a subject to be irradiated with the x-ray beams;
    said x-ray sources being movable along a line relative to the subject to execute tomosynthetic scanning of the subject with said x-ray beams, said x-ray sources being located next to each other along said line; and
    a two-dimensional x-ray detector disposed behind the subject, with respect to propagation of said x-ray beams, said x-ray detector detecting x-rays in said x-ray beams attenuated by the subject, said x-ray detector being disposed substantially stationary relative to the subject during said tomosynthetic scanning.

2. An x-ray system as claimed in claim 1 comprising a common housing containing both of said x-ray sources.

3. An x-ray system as claimed in claim 1 comprising a single x-ray tube containing both of said x-ray sources.

4. An x-ray system as claimed in claim 3 wherein said x-ray tube contains two anodes respectively for said two x-ray sources.

5. An x-ray system as claimed in claim 3 wherein said x-ray tube comprises an anode, said anode having different focal spots respectively for said two x-ray sources.

6. An x-ray system as claimed in claim 1 wherein said two x-ray sources are respectively operable to emit x-ray radiation of respectively different energies.

7. An x-ray system as claimed in claim 1 wherein said x-ray sources are movable through defined angle increments relative to the subject during said tomosynthetic scanning, with a distance between the two x-ray sources being equal to the angle increment or an integer multiple thereof.

8. An x-ray system as claimed in claim 1 wherein said x-ray sources are movable through an angle range relative to the subject during said tomosynthetic scanning, and wherein said x-ray sources are spaced apart by a distance equal to approximately half of said angle range.

9. An x-ray system as claimed in claim 1 wherein said two x-ray sources and said two dimensional x-ray detector are configured to implement mammography of a female breast as said subject, by said tomosynthetic scanning.

10. An x-ray system as claimed in claim 1 wherein said two x-ray sources are activatable independently of each other.

11. An x-ray system as claimed in claim 10 wherein said two x-ray sources are activatable in alternation, one at a time.

12. A method for tomosynthetic scanning of a subject, comprising:
    activating two x-ray sources emit an x-ray beam from each of said x-ray sources;
    irradiating a subject with the parallel x ray beams;
    moving said x-ray sources along a line relative to the subject to execute tomosynthetic scanning of the subject with said x-ray beams, and arranging said x-ray sources next to each other along said line;
    with a two-dimensional x-ray detector disposed behind the subject and substantially stationary relative to the subject, detecting x-rays in said x-ray beams attenuated by the subject during said tomosynthetic scanning; and
    generating an x-ray image from the x-rays detected by said x-ray detector.

13. A method as claimed in claim 12 comprising containing both of said x-ray sources in a common housing.

14. A method as claimed in claim 12 comprising employing a single x-ray tube containing both of said x-ray sources.

15. A method as claimed in claim 14 comprising configuring said x-ray tube with two anodes respectively for said two x-ray sources.

16. A method as claimed in claim 14 comprising providing said x-ray tube with an anode having different focal spots respectively for said two x-ray sources.

17. A method as claimed in claim 12 comprising respectively operating said two x-ray sources to emit x-ray radiation of respectively different energies.

18. A method as claimed in claim 12 comprising moving said x-ray sources through defined angle increments relative to the subject during said tomosynthetic scanning, with a distance between the two x-ray sources being equal to the angle increment or an integer multiple thereof.

19. A method system as claimed in claim 12 comprising moving said x-ray sources through an angle range relative to the subject during said tomosynthetic scanning, and spacing said x-ray sources apart by a distance equal to approximately half of said angle range.

20. A method as claimed in claim 12 comprising configuring said two x-ray sources and said two dimensional x-ray detector to implement mammography of a female breast as said subject, by said tomosynthetic scanning.

21. A method as claimed in claim 12 comprising independently activating said two x-ray sources.

22. A method as claimed in claim 21 comprising activating said two x-ray sources in alternation, one at a time.

* * * * *